United States Patent
Pate et al.

(10) Patent No.: US 7,056,496 B2
(45) Date of Patent: Jun. 6, 2006

(54) SUNSCREEN COMPOSITION AND A PROCESS FOR PREPARING IT

(75) Inventors: James E. Pate, North Greenfield, IN (US); Dale C. Schmidt, Midland, MI (US); David L. Malotky, Midland, MI (US); Anthony S. Drager, Midland, MI (US); Letha M. Gatz, Midland, MI (US); Christian Piechocki, Hauenau (FR)

(73) Assignee: Dow Global Technologies Inc., Midland, MI (US)

( * ) Notice: Subject to any disclaimer, the term of this patent is extended or adjusted under 35 U.S.C. 154(b) by 337 days.

(21) Appl. No.: 10/371,481

(22) Filed: Feb. 21, 2003

(65) Prior Publication Data

US 2003/0175316 A1    Sep. 18, 2003

Related U.S. Application Data

(63) Continuation-in-part of application No. 10/091,880, filed on Mar. 6, 2002, now Pat. No. 6,783,766.

(51) Int. Cl.
*A61K 7/42* (2006.01)
*A61K 7/44* (2006.01)
*A61K 7/00* (2006.01)

(52) U.S. Cl. ............ 424/59; 424/60; 424/400; 424/401

(58) Field of Classification Search ........... 424/59, 424/60, 400, 401
See application file for complete search history.

(56) References Cited

U.S. PATENT DOCUMENTS

| | | | |
|---|---|---|---|
| 4,018,426 A | 4/1977 | Mertz et al. | 259/7 |
| 4,446,127 A | 5/1984 | Bucheler et al. | 424/59 |
| 4,606,913 A | 8/1986 | Aronson | 424/59 |
| 4,934,398 A | 6/1990 | Chirinos et al. | 137/13 |
| 4,980,167 A | 12/1990 | Harashima et al. | 424/401 |
| 5,266,321 A | 11/1993 | Shukuzaki et al. | 424/401 |
| 5,387,417 A | 2/1995 | Rentsch | 424/401 |
| 5,412,004 A | 5/1995 | Tachibana et al. | 524/27 |
| 5,437,867 A | 8/1995 | Vichroski et al. | 424/401 |
| 5,539,021 A | 7/1996 | Pate et al. | 523/335 |
| 5,585,109 A | 12/1996 | Hayward et al. | 424/450 |
| 5,597,574 A | 1/1997 | Narayanan et al. | 424/401 |
| 5,599,533 A | 2/1997 | Stepniewski et al. | 424/78.02 |
| 5,654,362 A | 8/1997 | Schulz, Jr. et al. | 524/862 |
| 5,665,804 A | 9/1997 | Hill et al. | 524/268 |
| 5,688,842 A | 11/1997 | Pate, III et al. | 523/335 |
| 5,811,112 A | 9/1998 | Chandar et al. | 424/401 |
| 5,833,973 A | 11/1998 | Dobkowski et al. | 424/18.06 |
| 5,849,314 A | 12/1998 | Dobkowski et al. | 424/401 |
| 5,871,761 A | 2/1999 | Kuwata et al. | 424/401 |
| 5,874,105 A | 2/1999 | Watkins et al. | 424/450 |
| 5,919,437 A | 7/1999 | Lee et al. | 424/68 |
| 5,919,468 A | 7/1999 | Bara | 424/401 |
| 5,928,660 A | 7/1999 | Kobayashi et al. | 424/401 |
| 5,948,855 A | 9/1999 | Lin et al. | 524/837 |
| 6,024,944 A | 2/2000 | Hansenne | 424/59 |
| 6,027,738 A | 2/2000 | Stepniewski et al. | 424/401 |
| 6,039,935 A | 3/2000 | Mohammadi | 424/59 |
| 6,074,672 A | 6/2000 | Dobkowski et al. | 424/489 |
| 6,080,394 A | 6/2000 | Lin et al. | 242/78.03 |
| 6,083,900 A | 7/2000 | Auguste et al. | 512/2 |
| 6,103,250 A | 8/2000 | Brieva et al. | 424/401 |
| 6,126,948 A | 10/2000 | Simonnet et al. | 424/401 |
| 6,143,282 A * | 11/2000 | Hansenne et al. | 424/59 |
| 6,177,071 B1 | 1/2001 | Lin et al. | 424/78.03 |
| 6,177,091 B1 | 1/2001 | Bara et al. | 424/401 |
| 6,221,927 B1 | 4/2001 | Lin et al. | 521/64 |
| 6,221,979 B1 | 4/2001 | Lin et al. | 525/477 |
| 6,228,348 B1 | 5/2001 | Simon et al. | 424/59 |
| 6,235,292 B1 | 5/2001 | Bara et al. | 424/401 |
| 6,248,339 B1 | 6/2001 | Knitowski et al. | 424/401 |
| 6,406,684 B1 | 6/2002 | Fecht et al. | 424/65 |
| 2001/0022965 A1 | 9/2001 | Heger et al. | 424/59 |
| 2002/0143072 A1 | 10/2002 | Aust et al. | 516/98 |
| 2003/0026856 A1 | 2/2003 | Aust et al. | 424/725 |
| 2003/0175316 A1 | 9/2003 | Pate et al. | 424/401 |

FOREIGN PATENT DOCUMENTS

EP    0295886    1/1992

(Continued)

OTHER PUBLICATIONS

Clarson, S.J., *Siloxane Polymers*, PTR Prentice Hall, New Jersey, 1993, pp. 465-468, 567, 616-617.

(Continued)

*Primary Examiner*—Shelley A. Dodson

(57) ABSTRACT

The present invention includes a process of preparing an advanced cosmetic product by combining a high internal phase ratio (HIPR) emollient-in-water emulsion with a partial cosmetic formulation that typically contains water, a coloring agent, a fragrance, a rheology modifier, or a pH adjuster, or a combination thereof. The present invention also includes compositions directed to two particular subclasses of HIPR emollient-in-water emulsions, namely an HIPR silicone elastomer-in-water emulsion and an HIPR sunscreen-in-water emulsion and water-diluted dispersions thereof. The use of an HIPR emulsion of a cosmetic emollient provides a simple and flexible method of formulating the cosmetic product, due in part to the long shelf-stability of the HIPR emulsion (greater than 1 year), and the low quantity of water in the emulsion (typically less than 20% by volume based on the volume of emollient and water). The HIPR sunscreen-in-water emulsion can be formulated into an advanced cosmetic product with an improved sun protection factor (SPF) and critical wavelength.

13 Claims, No Drawings

FOREIGN PATENT DOCUMENTS

| | | |
|---|---|---|
| EP | 0545002 | 8/1992 |
| EP | 0242219 | 10/1992 |
| EP | 0732144 A1 | 9/1996 |
| EP | 0869142 | 10/1996 |
| EP | 0787758 A1 | 8/1997 |
| EP | 0829253 | 3/1998 |
| EP | 0917870 | 5/1999 |
| EP | 1020494 | 7/2000 |
| EP | 1057872 | 12/2000 |
| EP | 1069150 | 1/2001 |
| EP | 1163951 | 12/2001 |
| EP | 0848029 | 4/2002 |
| EP | 1048886 | 12/2002 |
| EP | 0934959 | 4/2003 |
| WO | WO 9421234 | 9/1994 |
| WO | WO 99/43297 | 9/1999 |
| WO | WO 01/54663 | 8/2001 |
| WO | WO 01/54663 A2 | 8/2001 |
| WO | WO 01/56238 | 8/2001 |
| WO | WO 01/70197 | 9/2001 |
| WO | WO 01/70270 | 9/2001 |
| WO | WO 02/03915 | 1/2002 |
| WO | WO 02/03925 | 1/2002 |
| WO | WO 02/03929 | 1/2002 |
| WO | WO 02/03931 | 1/2002 |
| WO | WO 02/03932 | 1/2002 |
| WO | WO 02/03933 | 1/2002 |
| WO | WO 02/03934 | 1/2002 |
| WO | WO 02/03935 | 1/2002 |
| WO | WO 02/03950 | 1/2002 |
| WO | WO 02/03951 | 1/2002 |
| WO | WO 02/03952 | 1/2002 |
| WO | WO 02/04004 | 1/2002 |

OTHER PUBLICATIONS

Becher, Paul, *Emulsions Theory and Practice*, Oxford University Press, New York, 2001, pp. 83-85.

Starch, Michael, "New Developments in Silicone Elastomers for Skin Care," Dow Coming, Form No. 27-1060A, 2002, pp. 1-8.

* cited by examiner

SUNSCREEN COMPOSITION AND A PROCESS FOR PREPARING IT

This application is a Continuation-in-part (CIP) of application Ser. No: 10/091,880, filed Mar. 6, 2002 now U.S. Pat. No. 6,783,766.

BACKGROUND OF THE INVENTION

The present invention relates to a process for preparing a cosmetic formulation and to a cosmetic formulation composition. More particularly, the present invention relates to a process for preparing a cosmetic formulation and to a cosmetic formulation composition utilizing a high internal phase ratio (HIPR) emollient-in-water emulsion, for example, wherein the emollient of the emulsion may be a silicone elastomer or a sunscreen agent.

Historically, cosmetic formulations have been prepared by emulsifying an oil phase with an aqueous phase matrix using a batch process, wherein the oil and water mixture is sheared in a large vessel. The oil phase, typically, includes a mixture of complex and varying oil-miscible ingredients and, consequently, batch-to-batch reproducibility of oil droplet size is often elusive. Moreover, processing time can be quite long and scale-up of the process from the benchtop to the manufacturing plant can be frustrating because tank-based processes often do not scale up in a linear fashion.

In WO 01/54663, Wilmott et al. disclose a possible solution to the problems associated with formulating personal care products by providing a substantially surfactant-free stable aqueous dispersion (that is, stable for at least two months), containing up to 70%, more preferably up to 50%, by weight of an oil phase, to which active ingredients can be added. This approach allows simple mixing of all ingredients, without the need for sub-phases or any special processing, to create a formulated cosmetic product. Nevertheless, there still remains an ever-increasing need to offer formulators more flexibility in controlling and fine tuning the properties of the final product, and to allow the formulators to use dispersions at their convenience.

For example, although there are various known processes for making sunscreens, there is still a need to make an unencapsulated sunscreen agent emulsion with an improved sun protection factor (SPF).

Organic sunscreen emulsions with a particle size of less than 2 microns are known in the art wherein the organic sunscreen is encapsulated and the effective sun protection factor is improved with respect to conventional formulations (Duncan Aust, "Sunscreen SPF Enhanced By Nano-Dispersion Technology Study," Rose Sheet, Jun. 4, 2001). Unencapsulated organic sunscreens of small size are known by templating on solid disperse polymers (U.S. Pat. No. 6,216,948) or Pickering emulsions (U.S. Patent Publication No. 20020160030). Dispersions of solid organic sunscreens less than 2 microns have been made by grinding (micronizing) the solid sunscreen (U.S. Pat. No. 5,980,872). The use of an effective amount of a surfactant for making unencapsulated organic sunscreen emulsions less than 2 microns is not known.

As one objective of the present invention, it would be desirable to make unencapsulated organic sunscreen agents emulsions with emulsifying surfactants and a particle size less than 2 microns, preferably with improved SPF and critical wavelength.

SUMMARY OF THE INVENTION

The present invention addresses a need in the art by providing, in a first aspect, a process for preparing an advanced cosmetic product comprising the step of contacting a high internal phase ratio (HIPR) emollient-in-water emulsion with a partial cosmetic formulation to produce the advanced cosmetic product.

The process of the present invention reduces significantly the amount of water initially added to the formulated product, thereby providing a distinct advantage to the formulator for controlling the texture, sensation, consistency, shelf stability, and deliverability of active agents of the cosmetic product.

In a second aspect, the present invention is a composition comprising an HIPR silicone elastomer-in-water emulsion.

In a third aspect, the present invention is a composition comprising an HIPR sunscreen agent-in-water emulsion, wherein the sunscreen agent contains at least one chromophoric group absorbing in the ultraviolet range from 290 nanometers (nm) to 400 nm.

In the fourth aspect, the present invention is a stable emollient and water emulsion sunscreen concentrate composition which includes (a) water; (b) at least one emollient, wherein said emollient contains at least one sunscreen agent; and (c) at least one stabilizing amount of an emulsifying surfactant; wherein the concentrate is at least 55 percent (%) by weight sunscreen agent, based on the weight of the total composition.

A fifth aspect of the present invention is a composition comprising an unencapsulated sunscreen agent-containing emollient-in-water emulsion with a particle size of less than 3 microns, preferably less than 2 microns, and an effective amount of an emulsifying surfactant. The sunscreen composition of the present invention advantageously exhibits improved SPF and/or critical wavelength over conventional sunscreen formulations.

DETAILED DESCRIPTION OF THE INVENTION

In the process of the present invention, a high internal phase ratio (HIPR) emollient-in-water emulsion is contacted with a partial cosmetic formulation to produce an advanced cosmetic product. In general, HIPR emulsions are characterized by a disperse phase of polyhedral cells at a volume fraction of at least 74% (the most compact arrangement of spheres of equal radius) dispersed in a continuous phase that forms a thin film separating the cells.

As used herein, the word "emollient" refers to one or more water-immiscible substances used in cosmetic formulations; the term "water-immiscible substance" refers to a compound capable of forming an HIPR emulsion with water. Examples of emollients include i) mineral oil, petrolatum, polydecene, and isohexadecane; ii) fatty acids and alcohols having from 10 to 30 carbon atoms such as pelargonic, lauric, myristic, palmitic, steraric, isostearic, hydroxystearic, oleic, linoleic, ricinoleic, arachidic, behenic, and euricic acids and alcohols; iii) triglyceride esters such as castor oil, cocoa butter, safflower oil, sunflower oil, jojoba oil, cottonseed oil, corn oil, olive oil, cod liver oil, almond oil, avocado oil, palm oil, sesame oil, squalene, Kikui oil, and soybean oil; iv) acetoglyceride esters such as acetylated monoglycerides; v) ethoxylated glycerides such as ethoxylated glyceryl monostearate; vi) alkyl esters of fatty acids having 10 to 20 carbon atoms such as hexyl laurate, isohexyl laurate, isohexyl palmitate, isopropyl palmitate, decyl oleate, isodecyl oleate, hexadecyl stearate, decyl stearate, diisopropyl adipate, diisohexyl adipate, diisopropyl sebacate, laurly lactate, myristyl lactate, and cetyl lactate; vii) alkenyl esters of fatty acids having 10 to 20 carbon atoms such as oleyl myristate, oleyl stearate, and oleyl oleate; viii) fatty acid esters of ethoxylated fatty alcohols; ix) polhydric alcohol esters such as ethylene glycol mono and di-fatty acid esters, diethylene glycol mono- and di-fatty acid esters, and polyethylene glycol (for example, with a molecular weight of 200 to 6000) mono- and di-fatty acid esters; x) wax esters such as beeswax, spermaceti, myristyl myristate, and stearyl stearate; xi) silicone oils such as dimethicones and cyclomethicones; and xii) mixtures thereof.

Silicone elastomers constitute yet another class of emollients. These elastomers are advantageously prepared from the crosslinking reaction of a divinyl compound and a polysiloxane compound containing Si-H groups. Examples of commercially available silicone elastomers include General Electric Silicone 1229 (available from General Electric Company) and Dow Corning 9040 Silicone Elastomer Blend (available from Dow Corning Corporation, Midland, Mich.).

For the purposes of the present invention, organic sunscreen agents are also emollients. An "organic sunscreen agent" herein means an agent which contains at least one chromophoric group that absorbs in the ultraviolet range of from 290 nm to 400 nm. Examples of chromophoric organic sunscreen agents include p-aminobenzoic acid as well as salts and esters thereof; o-aminobenzoic acid and o-aminobenzoates (including methyl, menthyl, phenyl, benzyl, phenylethyl, linalyl, terpinyl, and cyclohexenyl esters thereof); salicylic acid and salicylates (including octyl, amyl, phenyl, benzyl, menthyl, glyceryl, and dipropyleneglycol esters thereof); cinnamic acid and derivatives thereof (including menthyl and benzyl esters, alkyl alkoxycinnamates such as octyl methoxycinnamate (also known as 2-ethylhexyl-4-methoxycinnamate), alpha-phenyl cinnamonitrile, and butyl cinnamoyl pyruvate); dihydroxycinnamic acid and its derivatives; trihydroxycinnamic acid and its derivatives; diphenylbutadiene and stilbene; dibenzalacetone and benzalacetophenone; naphthosulfonates (such as sodium salts of 2-naphthol-3,6-disulfonic acid and 2-naphthnol-6,8-disulfonic acid); dihydroxynaphthoic acid and its salts; o- and p-hydroxydiphenyldisulfonates; coumarin and derivatives thereof (such as 7-hydroxy, 7-methyl, and 3-phenyl coumarin); diazoles; quinine salts; quinoline and derivatives thereof; hydroxy- or alkoxybenzophenones; uric and vilouric acids; tannic acid and derivatives thereof; hydroquinone; benzophenones (such as oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane); and mixtures thereof.

Examples of some commercially available sunscreen agents are listed in the following table.

| INCI Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |

-continued

| INCI Name | Trade Name | Supplier |
|---|---|---|
| Ethyl dihydroxypropyl PABA | AMERSCREEM P | Amerchol Corp. |
| Glyceryl PABA | NIPA G.M.P.A. | Nipa Labs. |
| Homosalate | EUSOLEX HMS | Rona/EMD Chemicals |
| Menthyl Anthranilate | NEO HELIOPAN MA | Haarmann & Reimer |
| Octocrylene | UNINUL N-539 | BASF Chemical Co. |
| Octyl dimethyl PABA | ESCALOL 507 | ISP |
| Octyl methoxycinnamate | PARSOL MCX | Roche Chemicals |
| PABA | PABA | Nipa Labs |
| 2-Phenyl-benzimidazole-5-sulfonic acid | EUSOLEX 232 | Rona/EMD Chemicals |
| TEA salicylate | NEO HELIOPAN TS | Haarmann & Reimer |
| 4-Methylbenzylidene camphor | EUSOLEX 6300 | Rona/EMD Chemicals |
| Benzophenone-1 | UVINUL 400 | BASF Chemical Co. |
| Benzophenone-2 | UVINUL D-50 | BASF Chemical Co. |
| Benzophenone-6 | UVINUL 3049 | BASF Chemical Co. |
| 5-Isopropyl-di-benzoylmethane | EUSOLEX 8020 | ona/EMD Chemicals |
| Etocrylene | UVINUL 3035 | BASF Chemical Co. |
| Octyl Salicylate | NEO HELIOPAN OS | Haarmann & Reimer |
| Avobenzone | PARSOL 1789 | Roche |

Typically, sunscreen-in-water emulsions may contain an additive to prevent Ostwald ripening, that is, to prevent diffusion of the sunscreen active disperse phase from small droplets of the disperse phase to larger ones. The HIPR sunscreen-in-water emulsion of the present invention advantageously may include a stabilizing amount of an additive to prevent Ostwald ripening, that is, to prevent diffusion of the sunscreen active disperse phase from small droplets of the disperse phase to larger ones. The additive used to prevent Ostwald ripening is a highly water-insoluble material that 1) has a negligible diffusion coefficient in the continuous aqueous phase and 2) is compatible with the disperse phase (for example, an emollient-phase compatible polymer such as polyisobutene; a long chain paraffin such as hexadecane; or a silicone such as silicone oil or dimethicone.) Preferably, the additive used to prevent Ostwald ripening is used in an amount not greater than 5 weight percent, and more preferably not greater than 2 weight percent, based on the weight of the sunscreen agent and the additive.

The HIPR sunscreen-in-water emulsion concentrate preferably has a volume mean particle size of less than 5 microns ($\mu$m), more preferably less than 3 $\mu$m, even more preferably less than 2 $\mu$m, and most preferably less than 1 $\mu$m.

The HIPR sunscreen agent-containing emollient-in-water emulsion concentrate is advantageously diluted with water to form a stable aqueous dispersion having an emollient content of at least 55% by weight, preferably at least 60% by weight, and more preferably at least 70% by weight, based on the weight of the water and the emollient. The concentrate may be used in a product at a level that conforms to typical Food and Drug Administration (FDA) allowed use levels.

It has been surprisingly discovered that unencapsulated emulsions of organic sunscreens can be made with conventional anionic and nonionic surfactants with a particle size of less than 3 microns. The sunscreen formulation also has the unanticipated properties of substantially increased SPF and/or increased critical wavelength.

It has been surprisingly discovered that an organic sunscreen agent-containing emollient-in-water emulsion concentrate having a small volume mean particle size exhibits a higher critical UV wavelength absorbance and a higher sun protection factor (SPF) than the same concentrate with a higher volume mean particle size. For example, the sunscreen composition of the present invention may provide a SPF increase of generally at least 20%, preferably at least 50% and more preferably at least 70%, when compared to a sunscreen composition having the same components, except that the sunscreen-containing emollient component has a volume mean particle size of greater than 3 microns. In addition, a sunscreen composition of the present invention may exhibit a critical wavelength increase of generally at least 10 nm, preferably 15 nm, and more preferably 20 nm, when compared to a sunscreen composition having the same components, except that the sunscreen-containing emollient component has a volume mean particle size of greater than 3 microns.

For example, an octyl methoxycinnamate (OMC) sunscreen emulsion exhibits both an increase in SPF and critical wavelength even in the absence of 1) UVA enhancement additives having a critical wavelength of greater than 350 nm, such as, for example, zinc oxide, or 2) UVA boosters that cause the OMC to shift its critical wavelength to greater than 350 nm, such as, for example, polar solvents such as ethanol, or 3) SPF boosters such as, for example, tricontanyl PVP or titanium oxide. Although it is possible to include one or more UVA or SPF enhancement additives or UVA or SPF boosters in the OMC-in-water concentrate, it is preferred not to for reasons of cost, reduced irritation and photostability. If, however, UVA or SPF enhancement additives or UVA or SPF boosters are used, the total concentration of additives and boosters is less than 30% by weight, preferably less than 20% by weight, more preferably less than 10% by weight, even more preferably less than 5% by weight, and most preferably less than 1% by weight of the UVA or SPF enhancement additive or UVA or SPF booster additives, based on the total weight of the sunscreen agent (such as OMC), the enhancement additives, the boosters and any other emollients.

The HIPR emollient-in-water emulsion is stabilized by a stabilizing amount of a surfactant. The surfactant employed may be internal (that is, wherein the emollient itself acts as a surface active agent) or external (that is, wherein the surfactant is added as a separate component). The concentration of the surfactant is preferably not less than 1% by weight, and more preferably not less than 3% by weight; and preferably the surfactant is not more than 20% by weight, and more preferably not more than 10% by weight, based on the weight of the emollient phase. External surfactants include, for example, nonionic, anionic, cationic or zwitterionic surfactants, or any combinations thereof.

Examples of nonionic surfactants suitable for stabilizing the HIPR emulsion include polyethylene glycol fatty acid mono- and diesters (such as PEG-8 laurate, PEG-10 oleate, PEG-8 dioleate, and PEG-12 distearate); polyethylene glycol glycerol fatty acid esters (such as PEG-40 glyceryl laurate and PEG-20 glyceryl stearate); alcohol-oil transesterification products (such as PEG-35 castor oil, PEG-25 trioleate, and PEG-60 corn glycerides); polyglycerized fatty acids (such as polyglyceryl-2-oleate and polyglyceryl-10 trioleate); propylene glycol fatty acid esters (such as propylene glycol monolaurate); mono- and diglycerides (such as glyceryl monooleate and glyceryl laurate); sterol and sterol derivatives (such as cholesterol); sorbitan fatty acid esters and polyethylene glycol sorbitan fatty acid esters (such as sorbitan monolaurate and PEG-20 sorbitan monolaurate); polyethylene glycol alkyl ethers (such as PEG-3 oleyl ether and PEG-20 stearyl ether); sugar esters (such as sucrose monopalmitate and sucrose monolaurate); polyethylene glycol alkyl phenols (such as PEG-10-100 nonyl phenol, and PEG-15-100 octyl phenol ether); polyoxyethylene-polyoxypropylene block copolymers (such as poloxamer 108 and poloxamer 182); lower alcohol fatty acid esters (such as ethyl oleatea and isopropyl myristate); and any combinations thereof.

Examples of suitable ionic surfactants include fatty acid salts (such as sodium laurate and sodium lauryl scarcosinate); bile salts (such as sodium cholate and sodium taurocholate); phosphoric acid esters (such as diethanolammonium polyoxyethylene-10 oleyl ether phosphate); carboxylates (such as ether carbokylates and citric acid esters of mono and diglycerides); acyl lactylates (such as lactylic esters of fatty acids, and propylene glycol aginate); sulfates and sulfonates (such as ethoxylated alkyl sulfates, alkyl benzene sulfones, and acyl taurates); alkyl, aryl, and alkyl-aryl sulfonates and phosphates; and any combinations thereof.

Examples of suitable cationic surfactants include quaternary ammonium salts and hydrochloride salts of N-alkyl diamines and triamines; and any combinations thereof.

The above surfactants may also be useful as the emulsifying surfactant for the organic sunscreen agent-containing emollient-in-water emulsion.

The HIPR emulsion can be prepared by a variety of methods, including batch and continuous methods well-known in the art. In a preferred continuous method (described generally by Pate et al. in U.S. Pat. No. 5,539,021, column 3,line 15 to column 6,line 27, which passage is incorporated herein by reference), a first stream containing a continuous aqueous phase is flowed through a first conduit and merged continuously with a second stream of a dispersed emollient phase that is flowed through a second conduit. The first and second streams are merged into a disperser in the presence of a stabilizing amount of surfactant. The surfactant can be added to either the first or second stream, or as a separate third stream, but is preferably added to the stream containing the emollient phase. The rates of the streams are adjusted within the HIPR emulsion region (74% to about 99%) so that the particle size and the polydispersity of the emulsion are optimized for the particular application. Preferably, the rates of the streams are adjusted so as to produce an HIPR emulsion having an emollient phase-to-aqueous phase ratio of from about 80% to about 95% by volume. The volume mean particle size of the emollient phase of the HIPR emulsion is application dependent. Though volume mean particle sizes of less than 1 μm are routinely achievable using the present invention, submicron particle sizes may not be desirable in all cases. Generally, the volume mean particle size of the emollient phase of the HIPR emulsion is not greater than 50 μm, preferably not greater than 20 μm, more preferably not greater than 10 μm, and even more preferably not greater than 2 μm. However, when the emollient is a silicone elastomer, the desired volume mean particle size is generally not less than 2 μm, preferably not less than 10 μm, and more preferably not less than 20 μm; and generally the volume mean particle size is not greater than 100 μm, and preferably not greater than 60 μm.

In another embodiment, when the emollient is a sunscreen agent, the sunscreen agent-containing emollient generally has a volume mean particle size of less than 3 microns, preferably, a volume mean particle size of less than 2 microns, and more preferably, a volume mean particle size of less than 1 micron.

If the preferred method used for preparing the HIPR emulsion is a continuous method, the emollient phase must be flowable through a conduit. If the emollient is sufficiently low in viscosity so as to be flowable at ambient temperature and without dilution of solvent, the HIPR emulsion is preferably prepared at ambient temperature and without the use of an ancillary solvent for the emollient. If, on the other hand, the emollient is not flowable through a conduit at ambient temperature, either because the emollient is a solid or a highly viscous liquid at ambient temperature, the emollient can be rendered flowable by either heat or solvent addition. For example, where the emollient is a silicone elastomer, it is desirable to add a solvent for the elastomer in a sufficient amount so as to render the silicone elastomer flowable through a conduit. Preferred solvents for the silicone elastomer include, for example, cyclomethicones, dimethicones, or other emollients.

Minor amounts, such as, for example, not greater than 5%, preferably not greater than 1%, and more preferably not greater than 0.5% by weight, of water-compatible substances, that is, substances which, by themselves are incapable of forming aqueous HIPR emulsions, can be added to the emollient prior to emulsification of the emollient. Examples of such water-compatible substances include rheology modifiers such as carbomers, acrylic copolymers, polyacrylamides, polysaccharides, natural gums, and clays; preservatives such as alkyl esters of p-hydroxybenzoic acid; humectants such as glycerol; pH modifiers; and mixtures thereof.

The HIPR emulsion used in the process of the present invention may be combined with a partial cosmetic formulation to produce an advanced cosmetic product. As used herein, "partial cosmetic formulation" refers to one or more finishing ingredients, which, when combined with the HIPR emulsion, form an advanced, and preferably a finished, cosmetic product. The term "advanced cosmetic product" refers to either a finished cosmetic product or one that is closer to being a finished product than before the HIPR emulsion and partial cosmetic formulation were combined. Preferably, the advanced cosmetic product is a finished cosmetic product that is ready to be packaged for and sold to the consumer. In an extreme case, the HIPR emulsion may contain all of the ingredients of the finished product, and the partial cosmetic formulation is simply water. In this case, the HIPR emulsion represents a concentrate of the finished product, which is merely diluted with water to form the finished product.

It is possible to prepare an HIPR emulsion that includes ingredients commonly found in a partial cosmetic formulation such as color, fragrance, rheology modifier, pH adjuster, and other ingredients such as active agents, aesthetics modifying agents, and adjuvants as described in WO 01/54663, page 15 to page 22, incorporated herein by reference. However, it may be desirable to exclude the above ingredients from the HIPR emulsion. For example, color, fragrance, rheology, or pH may be more easily controlled when included in the partial cosmetic formulation and combined with an HIPR emulsion that contains predominantly the emulsfied emollient. The HIPR emulsion and the partial cosmetic formulation can be combined concomitantly or in any order. Furthermore, more than one HIPR emulsion can be combined with the partial cosmetic formulation to form the advanced cosmetic product. For example, an HIPR emulsion of mineral oil and a separately prepared HIPR emulsion of petrolatum can be combined with a partial cosmetic formulation containing water, thickener, fragrance, and color to form a body lotion. Examples of finished cosmetic products include hand lotions, body lotions, body washes, conditioners, shampoos, facial creams, facial lotions, facial masks, and fully formulated sunscreens.

The process of the present invention provides a simple and flexible method of formulating the cosmetic product, due to the ease with which an HIPR emulsion with controlled particle size can be reproduced, due to the long shelf-stability of the HIPR emulsion (greater than 1 year), and due to the low quantity of water in the emulsion (for example, less than 26%, and preferably less than 20% by volume, based on the volume of emollient and water).

The following examples are for illustrative purposes only and are not intended to limit the scope of the present invention. All percentages are by weight unless otherwise specified. Particle sizes of HIPR emulsions are measured using a particle size analyzer such as a Beckman Coulter LS 230 Particle Size Analyzer (Beckman Coulter Inc.). SPF and critical wavelength are measured using a standard UV analyzer instrument such as a Labsphere UV Analyzer (Labsphere Inc.).

EXAMPLE 1

Procedure for Preparing a Concentrated Silicone Elastomer Emulsion

An HIPR emulsion containing Dow Corning 9040 Silicone Elastomer Blend was prepared in the following manner. First, Dow Corning 345 Fluid (19.5%) and TERGITOL 15-s-12 (a trademark of The Dow Chemical Company, 2.4%, secondary alcohol ethoxylate surfactant) was added to the Dow Corning 9040 Silicone Elastomer Blend (78.1%). The ingredients were then mixed until uniform in a vessel with both sweep and helical agitation. This disperse phase was pumped by a Zenith gear pump at a rate of 30 grams per minute (g/min) through a ½-inch stainless steel tubing into a four-inch diameter Oakes rotor stator mixer spinning at 800 revolutions per minute (rpm). The disperse phase was merged at the mixer with a separate deionized water stream phase containing a DOWICIL 200 antimicrobial (a trademark of The Dow Chemical Company, 0.05% based on the weight of the water). This continuous water phase was pumped into the mixer through a ¼-inch stainless steel tubing using an Alltech liquid chromatography pump at a rate of 5.7 g/min. The resultant emollient phase of the HIPR emulsion was 82 weight %, based on the weight of all of the materials in the HIPR emulsion (65.6 weight % of the silicone elastomer and 16.4 weight percent of Dow Corning 345 Fluid). The resultant HIPR emulsion had a volume mean particle size of 30 microns (μm).

EXAMPLE 2

Procedure for Making a Concentrated Silicone Elastomer Emulsion

An HIPR emulsion containing Dow Corning 9040 Silicone Elastomer Blend was prepared in the following manner. First, Mirasil 500,000 centistoke silicone fluid (7%) was added to the Dow Corning 9040 Silicone Elastomer Blend (93%) and heated to 70° C. The ingredients were then mixed until uniform with a bench top mixer at 70° C. This disperse phase was pumped by a Zenith gear pump at a rate of 22 g/min through a ½-inch stainless steel tubing into a four-inch diameter Oakes rotor stator mixer spinning at 800 rpm. The rotor used had every other tooth removed on both sides. The disperse phase was merged at the mixer with a separate deionized water phase containing Rhodapex ES2 surfactant (28% active, 57% based on the total weight of the water phase). This continuous water phase was pumped into the mixer through a ¼-inch stainless steel tubing using an Alltech liquid chromatography pump at a rate of 3.5 g/min. The resultant HIPR emulsion was 81 wt % Dow Corning 9040 Silicone Elastomer Blend based on the weight of all the materials in the emulsion, and had a volume mean particle size of 24μm.

EXAMPLE 3

Procedure for Making a Finished Product Using an HIPR Triglyceride Emulsion

A. Preparation of HIPR Triglyceride Emulsion

The emollient phase for an HIPR triglyceride emulsion was prepared by melting TERGITOL 15-s-15 surfactant (2.5%) at 50° C. and adding the surfactant to triglyceride (96.4%), which had also been heated to 35° C. The material was then mixed for five minutes with a propeller mixer while maintaining a temperature at 35° C. Next, 0.5 wt % Hamposyl L-30 surfactant (30% active) and 0.21% DOWANOL EPh glycol ether (a trademark of The Dow Chemical Company), low phenol grade were mixed into the triglyceride with the propeller mixer. This disperse phase was pumped by a Zenith gear pump at a rate of 30 g/min through a ½-inch stainless steel tubing into a four-inch diameter Oakes rotor stator mixer spinning at 500 rpm. The disperse phase was merged at the mixer with a separate deionized water stream phase containing DOWANOL EPh glycol ether (2.4% based on the weight of the water). This continuous water phase was pumped into the mixer through a ¼-inch stainless steel tubing using an Alltech liquid chromatagraphy pump at a rate of 1.5 g/min. The resultant HIPR emulsion had a volume mean particle size of 0.84 μm and is 92% triglyceride by weight based on the weight of all the materials in the emulsion.

B. Preparation of Finished Product

The resultant concentrated triglyceride emulsion prepared in Part A above, was incorporated into a partial cosmetic formulation as follows. Deionized water (177.15 grams (g)), glycerin (15.0 g), trisodium ethylene diamine tetra acidic acid (EDTA, 0.3 g), DOWICIL 200 antimicrobial (0.3 g) and concentrated triglyceride emulsion (30 g of 92% triglyceride) were placed in a 2-quart mixing bowl. The mixture was blended until uniform using a "flat beater" blade attachment on a KitchenAid mixer with a speed setting of 2. The mixer speed was then decreased to 1 and a 2% aqueous dispersion of Carbopol 980 carbomer (75 g) was added to the mixture. Once the mixture was homogeneous, triethanol amine (1.5 g), fragrance (0.75 g) and 2 drops of a 3% aqueous solution of food dye were added to the mixture. The resultant finished product was mixed until smooth. The resultant finished product showed a volume mean particle size of 0.85 μm.

EXAMPLE 4

Procedure for Making a Finished Product Using an HIPR Petrolatum-in-Water Emulsion and an HIPR Jojoba Oil-in-Water Emulsion A. Preparation of HIPR Petrolatum Emulsion The oil phase for a concentrated petrolatum emulsion was created by melting 3.6% Brij 721 surfactant and 2.4% Brij 72 surfactant at 75° C. and adding these materials to 94% petrolatum, which had also been heated to 75° C. The combined material was then mixed for five minutes with a propeller mixer while maintaining a temperature of 75° C. This disperse phase was pumped by a Zenith gear pump at a rate of 30 g/min through ½-inch stainless steel tubing into a four-inch diameter Oakes rotor stator mixer spinning at 1800 rpm. The disperse phase was merged at the mixer with a separate deionized water phase containing DOWANOL EPh glycol ether (low phenol grade, 2.4% based on the total weight of the water phase) and Hamposyl L-30 surfactant (30% active, 21% based on total weight of the water phase). This continuous water phase was pumped into the mixer through a ¼-inch stainless steel tubing using an Alltech liquid chromatography pump at a rate of 2.0 g/min. The resultant HIPR emulsion had a volume mean particle size of 0.95 μm. This petrolatum HIPR emulsion wass diluted in a centrifugal pump spinning at 500 rpm with a water stream identical to the first pumped at a rate of 2.5 g/min through a ¼-inch stainless steel tubing using a Milroyal piston pump. This resultant HIPR emulsion was 80% by weight petrolatum based on the weight of all the materials in the emulsion.

B. Preparation of HIPR Jojoba Oil Emulsion

The disperse phase for a HIPR jojoba oil emulsion was created by melting Brij 97 surfactant (4%) at 35° C. and adding it to jojoba oil (96%), which is also heated to 35° C. The material was then mixed for five minutes with a propeller mixer while maintaining a temperature of 35° C. This disperse phase was pumped by a Zenith gear pump at a rate of 30 g/min through ½-inch stainless steel tubing into a four-inch diameter Oakes stator rotor mixer spinning at 800 rpm. The disperse phase was merged at the mixer with a separate deionized water stream phase containing DOWICIL 200 antimicrobial (0.05% based on weight of the water phase). This continuous water phase was pumped into the mixer through a ¼-inch stainless steel tubing using an Alltech liquid chromatagraphy pump at a rate of 1.2 g/min. The resultant HIPR emulsion had a volume mean particle size of 1.01 μm. This jojoba oil HIPR emulsion was diluted in a centrifugal pump spinning at 500 rpm with a water stream identical to the first pumped at a rate of 3.2 g/min through a ¼-inch stainless steel tubing using a Milroyal piston pump. The resultant HIPR contained 83 wt % jojoba oil.

C. Preparation of Finished Product

Both HIPR emulsions prepared in Parts A and B above were added to a partial cosmetic formulation as follows. Deionized water (156.15 g), glycerin (15.0 g), trisodium EDTA (0.3 g), DOWICIL 200 antimicrobial (0.3 g), HIPR (83%) jojoba oil emulsion (15 g) and HIPR (92%) petrolatum emulsion (36 g) were placed in a 400 mL plastic beaker. The mixture was blended until uniform using a 2-inch Cowles blade attachment on a CAFRAMA mixer with a speed of 300 rpm. The mixer speed was then decreased to 150 rpm and a 2% aqueous dispersion of Carbopol 980 carbomer (75 g) was added to the mixture. Once the mixture was homogeneous, triethanol amine (1.5 g), fragrance (0.75 g) and food dye (2 drops of a 3% aqueous solution) was added to the mixture. The resultant finished product was mixed until smooth. The resultant finished product had a volume mean particle size of 1.02 μm.

EXAMPLE 5

Procedure for Making a Concentrated Octyl Methoxy Cinnamate Emulsion

A concentrated emulsion containing octyl methoxy cinnamate was prepared in the following manner. First, 200 g of potassium cetyl phosphate (Amphisol K) was combined with 200 g of propylene glycol and heated to 90° C. until the potassium cetyl phosphate had completely dissolved. Next, 360 g of this 50/50 cetyl phosphate/propylene glycol solution was combined with 180 g of polyoxyethylene (20) sorbitan monostearate (Tween 60), 60 g of 1,2,4-benzenetricarboxylic acid (Liponate TDTM) and 5400 g of octyl methoxy cinnamate (Parsol MCX). The ingredients were heated to 70° C. and mixed until uniform. The mixture was pumped by a ProMinent diaphram pump at a rate of 33 g/min through a ½-inch stainless steel tubing into a four-inch diameter Oakes rotor stator mixer spinning at 560 rpm. This stream was merged at the mixer with a separate deionized water stream phase containing Liquapar Optima preservative (2% based on the weight of the water). This water phase was pumped into the mixer through a ¼-inch stainless steel tubing using an Alltech liquid chromatography pump at a rate of 2.0 g/min. The resultant HIPR emulsion was 85% by weight octyl methoxy cinnamate, based on the weight of all the ingredients in the emulsion. The HIPR emulsion had a volume mean particle size of 0.6 μm as measured by a Beckman Coulter LS 230. The HIPR emulsion was diluted in a centrifugal pump spinning at 500 rpm with a water stream identical to the first pumped at a rate of 6.3 g/min through a ¼-inch stainless steel tubing using an Alltech liquid chromatography pump. This resultant emulsion was 72% by weight octyl methoxy cinnamate based on the weight of all the materials in the emulsion.

EXAMPLE 6

Procedure for Making an Octyl Methoxy Cinnamate Sunscreen from Concentrate

The concentrated octyl methoxy cinnamate emulsion from Example 5 was incorporated into a cosmetic product as follows. Deionized water (365 g), 2% Carbopol 980 solution (75 g) and disodium EDTA (0.5 g) were mixed together until uniform. Concentrated octyl methoxy cinnamate emulsion from Example 5 (52.1 g) was then added and mixed until uniform. Then, triethanolamine (2.4 g) and Germaben II preservative (5.0 g) were added to the mixture and the resultant product was mixed until smooth. The resultant finished lotion had an octyl methoxy cinnamate concentration of 7.5% and a volume mean particle size of 0.6 μm as measured by a Beckman Coulter LS 230.

The in-vitro SPF and critical wavelength of the finished lotion was measured using a Labsphere UV Analyzer. Prior to measurement of the lotion, the Analyzer was validated using a reference standard (5% homosalate emulsion). A total of 12 measurements were made. The average SPF value of the 12 measurements was 14.1, and the average critical wavelength of the 12 measurements was 364 nm.

Comparative Example A

A comparison cosmetic product was prepared as follows. Phase 1 was created by combining 376 g of deionized water, 75 g of 2% Carbopol 980 solution, 1.25 g of propylene glycol, and 1.25 g polyoxyethylene (20) sorbitan monostearate and heated to 85° C. while mixed until Phase 1 was uniform. Phase 2 was created by combining 1.25 g of potasium cetyl phosphate, 37.5 g octyl methoxy cinnamate, and 0.4 g of 1,2,4-benzenetricarboxylic acid and heated to 85° C. while mixed until this phase was uniform. Phase 2 was then added to Phase 1 while stirred with a Silverson mixer until the combined phase looked smooth and uniform.

Then, 3.5 g of triethanolamine was added to the combined phase. The combined phase was cooled to 45° C. and 3.5 g of Liquipar Optima preservative was added to the combined phase. The resultant finished lotion had an octyl methoxy cinnamate concentration of 7.5% and a volume mean particle size of 10 μm as measured by a Beckman Coulter LS 230.

The in-vitro SPF of the finished lotion was measured using a Labsphere UV Analyzer. Prior to measurement of the lotion, the Analyzer was validated using a reference standard (5% homosalate emulsion). A total of 10 measurements were made. The average SPF value of the 10 measurements was 7.1.

EXAMPLE 7

Procedure for Making a Concentrated Octyl Salicylate Emulsion

A concentrated emulsion containing octyl salicylate was prepared in the following manner. First, 100 g of potassium cetyl phosphate (Amphisol K) was combined with 100 g of propylene glycol and heated to 90° C. until the potassium cetyl phosphate had completely dissolved. Next, 180 g of this 50/50 cetyl phosphate/propylene glycol solution was ) combined with 90 g of polyoxyethylene (20) sorbitan monostearate (Tween 60), 30 g of 1,2,4-benzenetricarboxylic acid (Liponate TDTM) and 2700 g of octyl salicylate (Neo Heliopan OS). The ingredients were heated to 70° C. and mixed until uniform. The mixture was pumped by a ProMinent diaphram pump at a rate of 28.4 g/min through a ½-inch stainless steel tubing into a four-inch diameter Oakes rotor stator mixer spinning at 490 rpm. This stream was merged at the mixer with a separate deionized water stream phase containing Liquapar Optima preservative (1% based on the weight of the water). This water phase was pumped into the mixer through a ¼-inch stainless steel tubing using an Alltech liquid chromatography pump at a rate of 1.7 g/min. The resultant HIPR emulsion was 85% by weight octyl salicylate, based on the weight of all the ingredients in the emulsion. The emulsion had a volume mean particle size of 0.3 μm as measured by a Beckman Coulter LS 230. This HIPR emulsion was diluted in a centrifugal pump spinning at 550 rpm with a water stream identical to the first pumped at a rate of 10.5 g/min through a ¼-inch stainless steel tubing using an Alltech liquid chromatography pump. This resultant emulsion was 63% by weight octyl salicylate based on the weight of all the materials in the emulsion.

EXAMPLE 8

Procedure for Making an Octyl Salicylate Emulsion Sunscreen from Concentrate

The concentrated octyl salicylate emulsion from Example 7 was incorporated into a cosmetic product as follows. Deionized water (378 g), 2% Carbopol 980 solution (75 g) and disodium EDTA (0.5 g) were mixed together until uniform. Concentrated octyl salicylate emulsion from Example 7 (39.15 g) was then added to the mixture and mixed until uniform. Then, triethanolamine (2.4 g) and Germaben II preservative (5.0 g) were added to the mixture, and the resultant product was mixed until smooth. The resultant finished lotion has an octyl salicylate concentration of 5.0%.

The in-vitro SPF and critical wavelength of the finished lotion was measured using a Labsphere UV Analyzer. Prior to measurement of the lotion, the Analyzer was validated using a reference standard (5% homosalate emulsion). A total of 10 measurements were made. The average SPF value of the 10 measurements was 7.9,and the average critical wavelength of the 10 measurement was 358 nm.

EXAMPLE 9

Procedure for Making an Octyl Methoxy Cinnamate and Octyl Salicylate Emulsion Sunscreen from Concentrate The concentrated octyl methoxy cinnamate emulsion from Example 5 and the octyl salicylate from Example 7 were incorporated into a cosmetic product as follows. Deionized water (326 g), 2% Carbopol 980 solution (75 g) and disodium EDTA (0.5 g) were mixed together until uniform. Concentrated octyl methoxy cinnamate emulsion from Example 5 (52.1 g) and concentrated octyl salicylate emulsion from Example 7 (39.15 g) were then added to the mixture and mixed until uniform. Then, triethanolamine (2.15 g) and Germaben II preservative (5.0 g) were added to the mixture, and the resultant product was mixed until smooth. The resultant finished lotion had an octyl methoxy cinnamate concentration of 7.5% and an octyl salicylate concentration of 5.0%.

The in-vitro SPF and critical wavelength of the finished lotion was measured using a Labsphere UV Analyzer Prior to measurement of the lotion, the Analyzer was validated using a reference standard (5% homosalate emulsion). A total of 10 measurements were made. The average SPF value of the 10 measurements was 19.4, and the average critical wavelength of the 10 measurements was 361 nm.

EXAMPLE 10

Procedure for Making a Concentrated Octyl Methoxy Cinnamate, Octyl Salicylate and Benzophenone-3 Blend Emulsion A concentrated emulsion containing a blend of octyl methoxycinnamate, octyl salicylate and benzophenone-3 was prepared in the following manner. First, 250 g of potassium cetyl phosphate (Amphisol K) was combined with 250 g of propylene glycol and heated to 90° C. until the potassium cetyl phosphate had completely dissolved. Next, 480 g of this 50/50 cetyl phosphate/propylene glycol solution was combined with 240 g of polyoxyethylene (20) sorbitan monostearate (Tween 60), 80 g of 1,2,4-benzenetricarboxylic acid (Liponate TDTM), 3177 g of octyl methoxy cinnamate (Parsol MCX), 2118 g of octyl salicylate (Neo Heliopan OS), and 1906 g of benzophenone-3 (Escalol 567). The combined ingredients were heated to 70° C. and mixed until uniform. The mixture was then pumped by a ProMinent diaphram pump at a rate of 31 g/min through a ½-inch stainless steel tubing into a four-inch diameter Oakes rotor stator mixer spinning at 500 rpm. This stream was merged at the mixer with a separate deionized water stream phase containing Liquapar Optima preservative (1% based on the weight of the water). This water phase was pumped into the mixer through a ¼-inch stainless steel tubing using an Alltech liquid chromatography pump at a rate of 2.0 g/min. The resultant HIPR emulsion was 85% by weight the combination of octyl methoxy cinnamate, octyl salicylate and benzophenone-3, based on the weight of all the ingredients in the emulsion. The HIPR emulsion had a volume mean particle size of 0.5 µm as measured by a Beckman Coulter LS-230. This HIPR emulsion was diluted in a centrifugal pump spinning at 440 rpm with a water stream identical to the first pumped at a rate of 9.0 g/min through a ¼-inch stainless steel tubing using an Alltech liquid chromatography pump. This resultant emulsion was 66% by weight the combination of octyl methoxy cinnamate, octyl salicylate and benzophenone-3,based on the weight of all the materials in the emulsion.

EXAMPLE 11

Procedure for Making a Concentrated Avobenzone Emulsion

A concentrated emulsion containing avobenzone was prepared in the following manner. First, 1500 g of avobenzone (Parsol 1789) was combined with 2250 g of homosalate (Eusolex HMS), 2250 g of diethylhexyl 2,6-naphthalate (Corapan TQ), 300 g of polyoxyethylene (20) sorbitan monostearate (Tween 60), and 150 g of polyoxyethylene (20) cetyl/stearyl ether (Lipocol SC-20). The combined ingredients were heated to 80° C. while mixed until the avobenzone had completely dissolved. The mixture was then pumped by a ProMinent diaphram pump at a rate of 26 g/min through a ½-inch stainless steel tubing into a four-inch diameter Oakes rotor stator mixer spinning at 590 rpm. This stream was merged at the mixer with a separate deionized water stream phase containing Liquapar Optima preservative (1% based on the weight of the water). This water phase was pumped into the mixer through a ¼-inch stainless steel tubing using an Alltech liquid chromatography pump at a rate of 2.0 g/min. The resultant HIPR emulsion was 86% by weight the combination of avobenzone, homosalate and diethylhexyl 2,6-naphthalate, based on the weight of all the ingredients in the emulsion. The HIPR emulsion had a volume mean particle size of 0.6 µm as measured by a Beckman Coulter LS 230. This HIPR emulsion was diluted in a centrifugal pump spinning at 510 rpm with a water stream identical to the first pumped at a rate of 6.7 g/min through a ¼-inch stainless steel tubing using an Alltech liquid chromatography pump. This resultant emulsion was 70% by weight of the combination of avobenzone, homosalate and diethylhexyl 2,6-naphthalate, based on the weight of all the materials in the emulsion.

EXAMPLE 12

Procedure for Making a Concentrated Octyl Methoxy Cinnamate Emulsion

An HIPR emulsion containing octyl methoxy cinnamate was prepared in the following manner. First, 1.0% hydrogenated polyisobutene (Panalene L-14E), 2.0% polyoxyethylene (20) sorbitan monostearate surfactant (Tween 60) and 3% Hamposyl M-30 surfactant (a 30% aqueous solution, n-methyl, n-(1-oxotetradecyl) glycine sodium salt surfactant) were added to 94% octyl methoxy cinnamate (Parsol MCX). The combined ingredients were mixed until uniform in a vessel with both sweep and helical agitation. This resultant oil phase was then pumped by a Zenith gear pump at a rate of 34 g/min through a ½-inch stainless steel tubing into a four-inch diameter Oakes rotor stator mixer spinning at 800 rpm. The oil phase was merged at the mixer with a separate deionized water stream phase containing DOWI-CIL 200 antimicrobial (0.05% based on the weight of the water). This continuous water phase was pumped into the mixer through a ¼-inch stainless steel tubing using an Alltech liquid chromatography pump at a rate of 1.0 g/min. The resultant HIPR emulsion was 91% by weight octyl methoxy cinnamate, based on the weight of all the ingredients in the emulsion. The emulsion had a volume mean particle size of 1.0 μm.

What is claimed is:

1. A sunscreen composition comprising:
   A. an unencapsulated emollient-in-water emulsion containing water and at least one emollient, wherein the emollient of said emulsion contains at least one organic sunscreen agent, and wherein the sunscreen agent-containing emollient has a volume mean particle size of less than about 3 microns and the content of the sunscreen agent-containing emollient is at least 55% by weight, based on the weight of the water and the emollient; and
   B. an effective amount of an emulsifying surfactant to decrease the interfacial tension between water and the sunscreen agent.

2. A composition of claim 1 wherein the sunscreen agent-containing emollient has a volume mean particle size of less than about 2 microns.

3. A composition of claim 1 wherein the sunscreen agent-containing emollient has a particle size of less than about 1 micron.

4. A composition of claim 1 wherein the surfactant is anionic, nonionic or zwitterionic.

5. A composition of claim 1 wherein the sunscreen agent includes 2-ethylhexyl-4-methoxycinnamate.

6. A composition of claim 1 wherein the sunscreen agent includes octyl salicylate.

7. A composition of claim 1 wherein the sunscreen agent includes 2-ethylhexyl-4-methoxycinnamate and octyl salicylate.

8. A composition of claim 1 wherein the composition provides a sun protection factor (SPF) increase of at least about 20 percent when compared to a same sunscreen composition having Components A and B except that Component A contains a sunscreen agent-containing emollient having a volume mean particle of size greater than 3 microns.

9. A composition of claim 1 wherein the composition exhibits a critical wavelength increase of at least about 10 nm when compared to a same sunscreen composition having Components A and B except that Component A contains a sunscreen agent-containing emollient having a volume mean particle size greater than 3 microns.

10. A composition of claim 1 wherein the surfactant is selected from the group consisting of potassium cetyl phosphate, polyoxyethylene (20) sorbitan monostearate, 1,2,4-benzenetricarboxyic acid, tris(decyl) ester or any combination thereof.

11. A composition of claim 1 including an SPF enhancement additive, said SPF enhancement additive being different from the other components in the composition.

12. A composition of claim 1 including a UVA enhancement additive or a UVA booster, said UVA enhancement additive or UVA booster being different from the other components in the composition.

13. A process for preparing a sunscreen composition comprising mixing:
   A. an unencapsulated emollient-in-water emulsion, wherein the emollient contains at least one organic sunscreen agent, and wherein the sunscreen agent-containing emollient has a volume mean particle size of less than about 3 microns and the content of the sunscreen agent-containing emollient is at least 55% by weight, based on the weight of the water and the emollient; and
   B. an effective amount of an emulsifying surfactant to decrease the interfacial tension between water and the sunscreen agent.

* * * * *